United States Patent [19]

Delhaye et al.

[11] 4,195,930
[45] Apr. 1, 1980

[54] OPTICAL RAMAN MICROPROBE WITH LASER

[75] Inventors: Michel M. Delhaye; Paul A. Dhamelincourt, both of Villeneuve d'Ascq; Edouard F. da Silva, Lille, all of France

[73] Assignee: Agence Nationale de Valorisation de la Recherche (ANVAR), Neuilly-sur-Seine, France

[21] Appl. No.: 812,650

[22] Filed: Jul. 5, 1977

[30] Foreign Application Priority Data

Jul. 2, 1976 [FR] France ................................ 76 21539

[51] Int. Cl.$^2$ .............................................. G01J 3/44
[52] U.S. Cl. ..................................... 356/301; 350/91; 356/318
[58] Field of Search ..................... 356/73, 75, 85, 301, 356/318; 350/91

[56] References Cited

U.S. PATENT DOCUMENTS

| | | | |
|---|---|---|---|
| 3,718,400 | 2/1973 | Yenekubo | 356/73 |
| 4,030,827 | 6/1977 | Delhaye et al. | 356/75 |

*Primary Examiner*—Vincent P. McGraw
*Attorney, Agent, or Firm*—Frailey & Ratner

[57] ABSTRACT

An optical Raman microprobe with laser excitation for illuminating a sample, comprising means for illuminating the sample with a pulsed or continuous laser radiation of selected frequency, a microscope furnishing an enlarged image of the sample, means for selecting the wavelengths of the re-emitted or scattered light and means for detecting the selected light. The microprobe further comprises means for obtaining a micrographic image of the sample, to provide a map showing the distribution of a selected polyatomic species in the sample, by isolating a radiation characteristic of such species in the Raman, Stokes or anti-Stokes spectrum. All points of the sample may be illuminated simultaneously, or successively one after the other, or simultaneously along a selected line or curve. The apparatus may furnish the intensity curve of the Raman radiation along a selected straight line or curve, which permits a qualitative and quantitative analysis of the species selected, or it may furnish Raman spectra of very small, localized, selected regions within the image of the sample.

14 Claims, 16 Drawing Figures

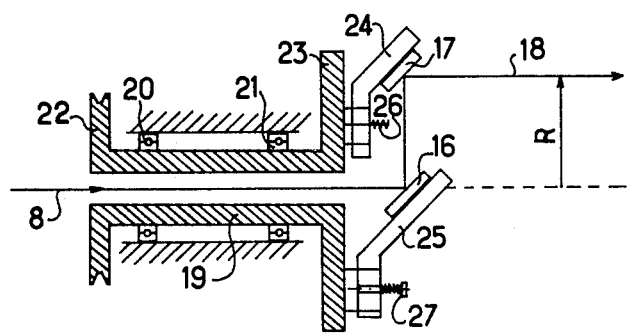
Fig. 4
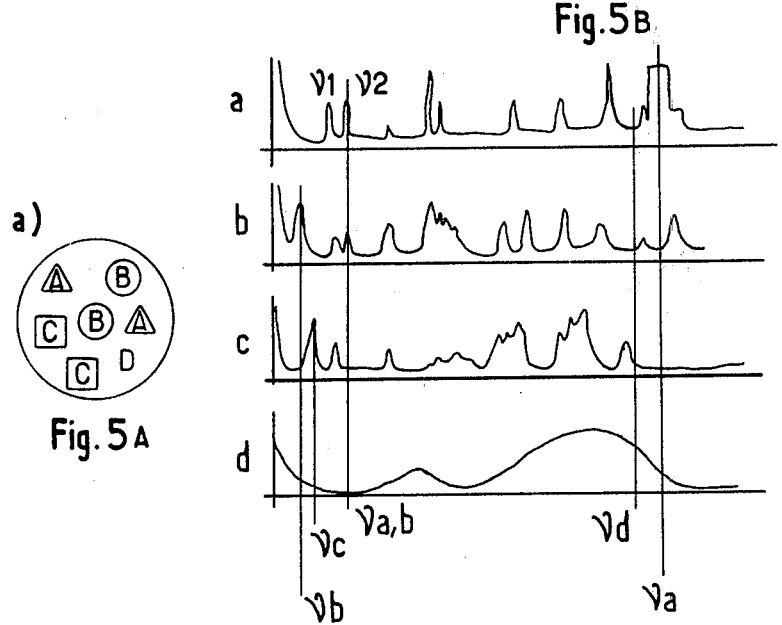
Fig. 5A
Fig. 5B

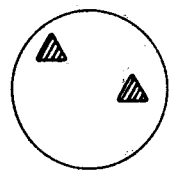
Fig.5C
νa
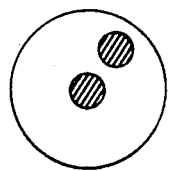
Fig.5D
νb
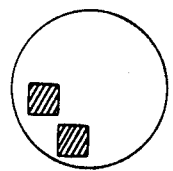
Fig.5E
νc
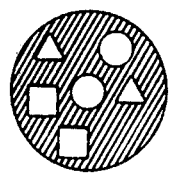
Fig.5F
νd
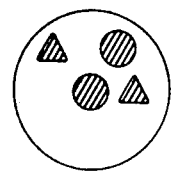
Fig.5G
νa,b
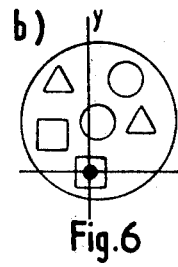
Fig.6
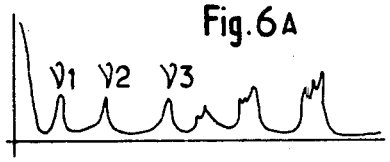
Fig.6A
Fig.6B
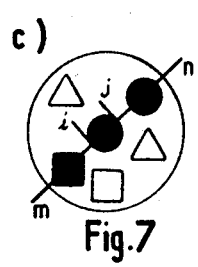
Fig.7
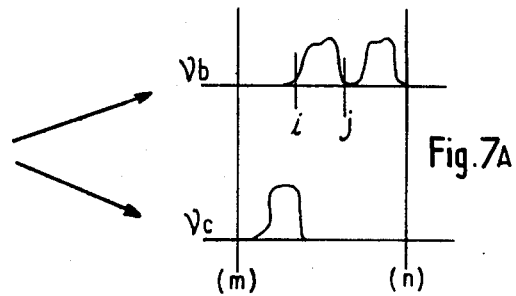
Fig.7A

OPTICAL RAMAN MICROPROBE WITH LASER

BACKGROUND OF THE INVENTION

The present invention relates to an improvement in an optical Raman microprobe with laser excitation for use in the non-destructive analysis of samples, particularly heterogeneous samples, with the aid of radiations re-emitted or scattered by the sample. Such a device has been disclosed in French Pat. No. 2,253,410 of Dec. 3, 1973 and in its counterpart U.S. Pat. No. 4,030,827. The device of those patents enables a micrographic image to be obtained, providing a map of the distribution in the sample of a particular polyatomic species, whether it be a molecule, a crystal or an ion, by isolating a radiation characteristic of such species in the Raman, Stokes or anti-Stokes spectrum.

It has been considered that different methods may be utilized to obtain information about a sample based on the Raman effect. According to the nature of the investigation desired to be made, one may seek to obtain
  either the above defined micrographic image with all points of the sample simultaneously illuminated,
  or the above identified micrographic image with points of the sample illuminated successively one after the other,
  or the intensity curve of the Raman radiation along a selected straight line or a curve within that image, which intensity curve, by comparison with reference data, permits the qualitative and quantitative analysis of the species in question.

Those methods have been described in various publications, including those submitted at the 18th Colloquium Spectroscopicum International at Grenoble in September of 1975, entitled: "Raman Microprobe and Microscope", pages 458 to 463. That publication is a document of general nature giving two principles of the microprobe described in French Pat. No. 2,253,410 aforesaid. Such methods have been disclosed, also, in the "Journal of Raman Spectroscopy", 1975, pp. 3.33–43 published by Reidel Publishing Company, of Dordrecht, Holland, the article being entitled "Raman Microprobe and Microscope with Laser Excitation". In the latter article, the authors provide very general explanations of the different modes of operation of the apparatus with the aid of block diagrams.

However, up until the present time, no apparatus has been able to carry out the three methods indicated above. Moreover, it may be useful, when studying a sample, to determine the nature of one of its components, as is done in conventional Raman spectroscopy.

SUMMARY OF THE INVENTION

The primary object of the present invention is to provide a unique Raman microprobe which includes mobile optical elements making it possible to obtain, according to their position:

(a) either a micrographic image providing a map of the distribution in a sample of a particular polyatomic species, whether it be a molecule, a crystal or an ion, obtained by isolating a radiation characteristic of such species in the Raman, Stokes or anti-Stokes spectrum, all points of the sample being simultaneously illuminated, (b) or a micrographic image providing a map of the distribution in a sample of a particular polyatomic species, whether it be a molecule, a crystal or an ion, obtained by isolating a radiation characteristic of such species in the Raman, Stokes or anti-Stokes spectrum, the points of the sample being illuminated one after the other, (c) or a micrographic image providing a map of the distribution in a sample of a particular polyatomic species, whether it be a molecule, a crystal or an ion, obtained by isolating a radiation characteristic of such species in the Raman, Stokes or anti-Stokes spectrum, the points of the sample being illuminated simultaneously along a selected straight line or curve within the image, (d) or the intensity curve of the Raman radiation along a selected straight line or curve within the image of the sample, which intensity curve enables a qualitative and quantitative analysis of the polyatomic species under consideration by comparison with reference data, (e) or Raman spectra of very small, localized, selected areas within the image of the sample.

The microprobe further includes means for detecting the selected light which are of the monochannel type, particularly a photomultiplier, and of the multichannel type, particularly an image intensifier.

More precisely, the mobile optical elements are:
a part of a condenser of the sample illuminating system, or the whole of such condenser,
a part of the optical transfer system located between the microscope and the wavelength selecting means, or the whole of such optical system,
a part of an optical transfer system located between the wavelength selecting means and the detection means, or the whole of such optical system,
and a mirror permitting the selected light to be directed either to a photomultiplier or to an image intensifier tube.

The invention is further characterized by the combination of:

(a) a source of pulsed or continuous monochromatic laser radiation of selected frequency;

(b) an optical device permitting several modes of illumination of a sample, either completely, or on a line or a point;

(c) a microscope to provide an enlarged image of the sample and having several possibilities for observing it, on a dark field, on a bright field, by reflection or by transmission;

(d) an optical transfer system which, by displacement of certain optical elements, forms such image as a function of the study undertaken either on the entrance slit of a monochromator or on the grating of a monochromator;

(e) an additive, at least double monochromator equipped with at least two concave holographic gratings whose surfaces are conjugated optically through the medium of a suitable optical system located at the level of an intermediate slit;

(f) an optical out-system forming, by displacement of certain optical elements, either the image of the surface of the second grating, or the image of the exit slit of the monochromator, on the photocathode of an image intensifier tube; and (g) an electronic detection means including photomultipliers, an image intensifier tube and a photographic or electronic camera, which permits the image of a sample or its spectrum to be visualized and its intensity curves to be recorded.

In certain cases, it will be advantageous to utilize a pulsed laser source and multichannel detection means in the form of an image intensifier tube.

The means for selecting the wavelength of re-emitted or scattered light makes it possible to isolate the characteristic Raman radiation and to eliminate the laser radiation diffused without change in wavelength at a rate of rejection at least equal to $10^{-10}$.

In order to select the wavelength of re-emitted light, an additive, at least double monochromator is used, provided with two concave holographic gratings having surfaces conjugated optically through the medium of a suitable optical system located at the level of an intermediate slit.

In one case, it is possible to examine the projection of intermediate images of the sample successively on the two gratings, and to examine the final image on the multichannel photoelectric receiver, the entrance pupil of the microscope being conjugated optically with the slits of the monochromator.

In a second case, it is possible to examine the projection of the intermediate images of the sample on the slits, the entrance pupil being conjugated optically with the gratings of the monochromator.

To avoid speckle noise, there is provided a device for illuminating a sample by laser beams, which interposes in the path of a fixed incident laser beam, originating from the laser source, a first inclined mirror which reflects said beam onto a second mirror inclined in a manner to reflect the laser beam toward the optical illumination system of the microscope, but shifted laterally with respect to the incident beam by a distance equal to the distance separating the two inclined mirrors. The two mirrors are rotatable about an axis concentric to the incident laser beam, so as to render uniform the illumination of the sample.

The apparatus further includes additional means for making other types of examinations. A mobile mirror is provided for the direct observation of the sample before the frequency selection. There is provided, also, means for illuminating the sample by transparency for the purpose of making diascopic examinations. Additionally, a mobile mirror is provided in the optical transfer system which, after rotation, permits the studying of several samples.

The microprobe also includes means for detecting rapidly and means for recording a series of images in the course of the development of a sample as a function of time during physico-chemical or biological reactions or transformations.

It is to be noted that, to obtain good results, it is preferable to utilize an efficient monochromator with gratings, specially designed for the study of the Raman effect, which may be a double or triple monochromator with flat or spherical gratings, engraved or holographic, Such monochromators are the subject matter of French patent applications 74.11.922 and 74.24.947. The latter application, filed July 12, 1974 in the name of Edouard da Silva, relates to a monochromator with slits having concave, holographic gratings. Application 74.11.922, filed Mar. 29, 1974 by the same applicant, relates to a spectrometer with coupled gratings.

If, for example, a double monochromator is used having two concave holographic gratings of 1,000 mm focal length and comprising 2,000 lines per millimeter, a filter will be obtained which will have the following features:

(a) a very low rate of stray light (even for large slits) in order to ensure a sufficient rejection of the laser radiation, (b) a suitable correction of astigmatism, (c) a high luminosity and (d) a transmission of the images without degradation of the spatial resolution of the microscope.

DESCRIPTION OF THE FIGURES OF THE DRAWING

The invention will be more readily understood from the following description, which provides a non-limiting practical example, and which is illustrated by reference to the accompanying drawing, in which:

FIG. 4 is an enlarged, detailed view in elevation showing a portion of the device for illuminating a sample.

FIG. 5a is a schematic representation of a sample (a).

FIG. 5b is a conventional Raman spectrum of the elements contained in the sample of FIG. 5a.

FIG. 5c is an overall image of the sample examined at frequency γa.

FIG. 5d is an overall image examined at frequency γb.

FIG. 5e is an overall image examined at frequency γc.

FIG. 5f is an overall image examined at frequency γd.

FIG. 5g is an overall image examined at frequency γab.

FIG. 6 is a schematic representation of a sample (b), the same being illuminated by a laser beam localized at a point XY.

FIG. 6a is the conventional Raman spectrum obtained from the illuminated sample of FIG. 6.

FIG. 6b is the multichannel image and spectrum obtained from the sample of FIG. 6.

FIG. 7 is a schematic representation of a sample (c), the laser beam being focused along the line mn.

FIG. 7a illustrates the intensity of distribution of the elements of the sample of FIG. 7 along the line mn.

DETAILED DESCRIPTION OF THE INVENTION

Figure 1:
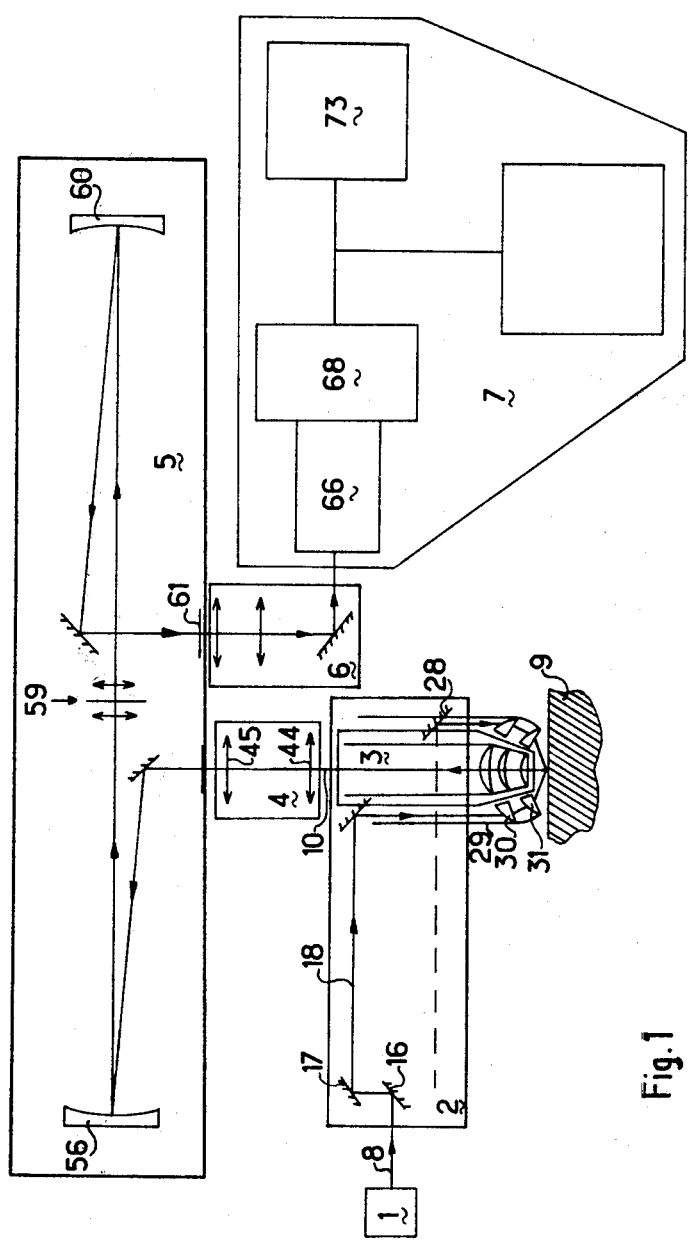
FIG. 1 is a schematic view of the apparatus of the invention.
Figure 2:
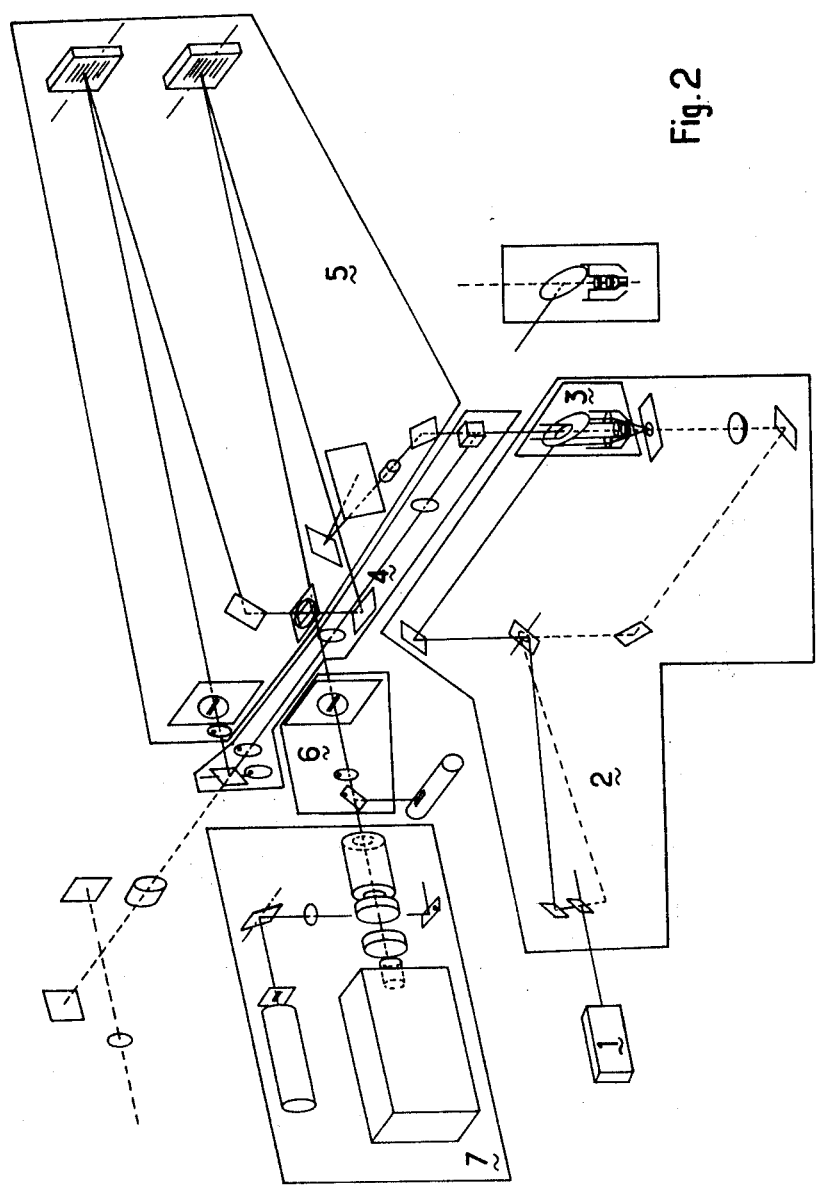
FIG. 2 is a perspective view of the apparatus of the invention, illustrating the main elements by block representation.

Referring now to FIGS. 1–4 of the drawing, the apparatus of this invention includes a source 1 of pulsed or continuous monochromatic laser radiation emitting a laser beam 8 toward a device 2 which permits several modes of sample illumination, and to which reference will be made further hereinafter. The laser radiation is received by the sample 9 and the radiation re-emitted thereby is examined by the microscope 3. The image leaving the microscope, shown schematically by the beam 10, may be examined on the control screen 11 (FIG. 3), after having passed through the separator prism 12, been reflected by mirror 13, passed into the projection lens 14 and been reflected by mirror 15. Alternately, the image, represented by beam 43, may be deflected by the separator prism 12 toward the optical transfer system 4 to be directed into the monochromator 5, at the exit point of which the radiation is collected in the optical out-system 6 from which it is directed to an electric detection means 7.

An important feature of the invention (FIG. 3) resides in the device 2 for illuminating the sample by laser beams, which renders uniform the illumination of the sample 9 by the selected incident laser beam 8 originating from the laser source 1. Device 2 includes a first inclined mirror 16 which reflects the beam 8 to a second mirror 17, which is inclined in such manner as to transmit the reflected beam 18 substantially parallel to the incident beam 8, i.e. in the same direction, but shifted laterally with respect thereto by a distance R (FIG. 4) equal to the distance between the two mirrors 16, 17.

The two mirrors 16 and 17 are mounted on a tubular support 19 (FIG. 4) which may be rotated on bearings 20 and 21 by a pulley 22. The support 19 includes a flange 23 on which are mounted, with capacity for adjustment, supports 24, 25 for the mirrors 17, 16, respectively. Adjustment of the supports 24, 25 is effected by means of screws 26, 27. The tubular support 19 is disposed concentric to the laser beam 8. By this arrangement, a reflected beam 18 is obtained which envelops a cone of revolution, the axis of which coincides with the incident beam 8.

The beam 18 scans an annular surface which includes the mirror 28 (FIG. 1) incorporated in the microscope 3. This permits the illumination of the sample 9 by the beam 18 passing through an outer tube 29, which is concentric to the microscope 3. Tube 29 includes annular lenses 30, 31, acting as a condenser. The annular illuminating means comprising mirror 28 and lenses 30, 31 permits the sample to be uniformly illuminated so as to obtain images therefrom free of speckle noise. The device 2 permits an overall illumination as well as a linear or a pin-point illumination of the sample 9.

In overall illumination, the laser beam 8 is reflected by the mirrors 16 and 17 which are continuously rotated by the tubular support 19 mounted on the bearings 20, 21. The reflected beam 18 is directed onto the mirrors 37 and 38 before being directed, in the form of beam 39 (or 35), into the microscope 3. In such case, the illumination is episcopic.

Figure 3:
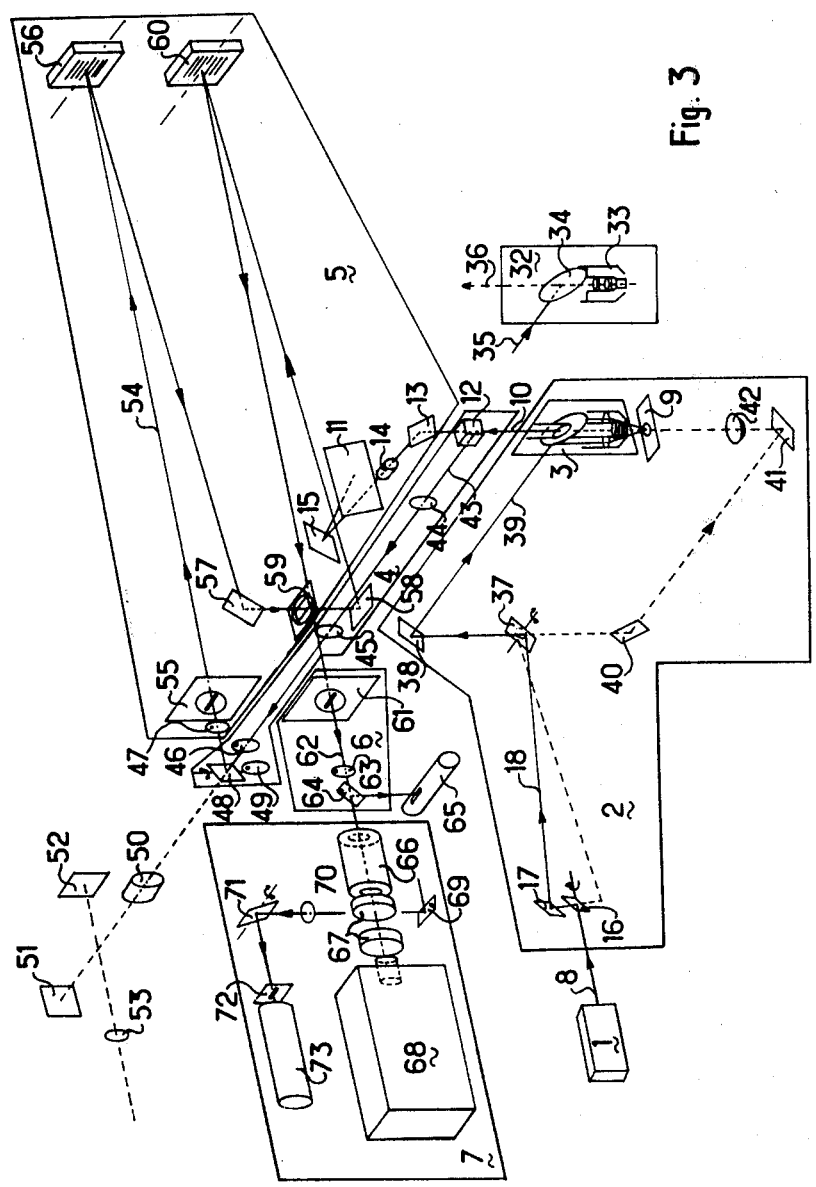
FIG. 3 is a detailed view similar to FIG. 2.

The modification represented by the frame 32 of FIG. 3 permits pin-point illumination of the sample 9 by means of the mirror 34 and the lens 33. In such case, the tubular support 19 mounting the mirrors 16 and 17 may be retracted, and the laser beam 35 is reflected by the mirror 34, then focused at the level of the sample 9 by the lens 33. Alternatively, after having been reflected by the mirrors 40 and 41, the laser beam, as shown by the broken lines in FIG. 3, may be focused at the level of the sample 9 by the condenser 42. In order to obtain a linear illumination of the sample, the pin-point of foculization obtained previously is rapidly deviated along a selected line, either straight or curved, by imparting a slight rocking movement to mirror 38 or 40. In such modifications, sample 9 may be illuminated by transparency (diascopic examination either on a dark field or a bright field).

In the case of such modifications, the path of the exit beam 36 is identical to that of exit beam 10 previously explained, and the same advantages are realized as in the arrangement for overall illumination described above.

When beam 43 is deflected from the separator prism 12, toward the optical transfer system 4, it passes through lenses 44, 45, 46 and either of lenses 47 or 49, a mobile mirror 48 being placed between lens 46 and the last two lenses 47 and 49. The mirror 48 directs the beam 43 toward the monochromator 5. Additionally, mirror 48 may receive a beam (shown in broken line in FIGS. 2 and 3) coming from a sample (not shown) external of the apparatus, through a focusing lens 53, mirrors 52 and 51 and transfer lens 50 which are part of a transfer plate external of the apparatus. The lens 53 and the mirror 52 permit the illumination of such sample, while mirror 51 and lens 50 extract the Raman radiations scattered by the sample.

The beam 54, which has just passed through the field lens 47 (or alternatively lens 49), enters the monochromator 5 through the slit 55. It then is sent to a first concave holographic grating 56, then to the two spaced mirrors 57, 58, between which is located a transfer lens placed on the intermediate slit 59 of the monochromator. From mirror 58, beam 54 passes to a second concave holographic grating 60, before passing through a slit and transfer lens 61 into the optical out-system 6. This results in a beam 62 characteristic of the Raman spectrum which may be detected by different means. The Raman beam 62, after passing the mobile lens 63, may be examined on the mirror 64 and the photomultiplier 65. By retracting the mirror 64, the Raman beam 62 may be projected directly onto the photocathode of the image intensifier tube 66. The resultant image is taken up by the image transfer lens 67 in order to be examined by the camera 68.

The extent of intensity may be determined with the aid of a mirror 69, which may send the image issuing from the intensifier tube 66 toward a photomultiplier 73 through a lens 70, a mobile mirror 71 and a slit 72.

An important feature of the invention resides in the fact that projection of intermediate images of the sample may be made:
either successively on the two gratings 56, 60, with the final image appearing on the intensifier tube 66, the entrance pupil of the microscope being conjugated optically with the slits 55, 59, 61,
or on the slits 55, 59, 61, the entrance pupil being conjugated optically with the gratings 56, 60.

These two modes of operation may be obtained by simple optical commutation (mirrors, lenses) inside the optical transfer system 4 and the optical out-system 6. In practice, the commutation occurs with the lenses 44, 45, 46, 47 or 49, 63. In particular, it is to be observed that the optical out-system 6, located after the exit slit 61, may project either the image or the spectra on the camera 68.

The illumination of the whole of the field associated with a multichannel detection system simultaneously registering all of the points of an image (micrography or Raman spectrum) permits the use of continuous or pulse lasers.

This novel assembly permits the study of the development of the sample as a function of time, for example, during the course of reactions of physico-chemical or biological transformations.

To illustrate different types of operations of the microprobe, a microscopic sample (a) may be selected (FIG. 5a) composed of different elements schematized as A, B, C, in a substrate D. Each element A, B, C, D possesses a characteristic Raman spectrum a, b, c, d (FIG. 5b). Each spectrum possesses characteristic frequencies $\gamma 1, \gamma 2, \ldots \gamma n$.

A frequency $\gamma a$ from the Raman spectrum of element A is chosen, which does not exist for the other elements B, C, D. After complete illumination of the sample, its Raman image is examined at the selected frequency $\gamma a$. Only the elements A are observed in the Raman image of the sample (FIG. 5c). Similarly, at frequency $\gamma b$, only the Raman image of elements B is observed, etc. . . . (FIGS. 5d, 5e, 5f).

At frequency γa, b, which corresponds to two characteristic lines of elements A and B, only elements A and B are obtained in the image (FIGS. 5b, 5g).

If the sample (b) (FIG. 6) includes an unknown element which is to be ascertained, the laser beam is focused on the element at the point XY. There is obtained the complete conventional monochannel spectrum or a part of the multichannel spectrum. By means of previous knowledge of the spectrum which characterizes the element, the unknown element in the sample (b) may be identified.

If the laser beam is focused on a line, the intensity of distribution of element B along the line mn of a sample (c) (FIG. 7) may be examined, using frequency γb which is characteristic of element B. Similary, at frequency γc, the intensity of distribution of element C in the sample (c) may be examined (FIG. 7a).

Similarly, the development of an image as a function of time, or the development of the intensity of a point or a line, may be examined in order to observe kinetics or physico-chemical or biological transformations.

The simultaneous illumination of a sample along a straight line or a curve is effected by selected movement of the illuminating means, particularly mirrors 16, 17, 37, 38, 40, 41, as well as by the interposition of optical or electro-optical elements.

Although preferred embodiments of this invention have been shown and described for the purpose of illustration, it is to be understood that various changes and modifications may be made therein, without departing from the spirit and utility of the invention, or the scope thereof as set forth in the claims.

We claim:

1. A Raman microprobe for the production of micrographic images of the distribution of the polyatomic species in a sample, obtained by isolating a radiation characteristic of a selected species chosen in the Raman, Stokes or anti-Stokes spectrum with all points of the sample being simultaneously illuminated, or with the sample being illuminated along a selected straight or curved line, or with selected points of the sample being illuminated by pin-point illumination, said microprobe also being adapted for obtaining the intensity curve of the Raman radiation along a selected straight or curved line of the sample and for obtaining the Raman spectra of very small localized selected areas of the sample, said microprobe including:
   (a) a source of pulsed or continuous laser radiation,
   (b) a sample illuminating device incorporating means for the selective illumination of a sample completely, or along a selected straight or curved line, or at a selected point,
   (c) a microscope for providing an enlarged image of the sample,
   (d) an optical transfer system having mobile optical elements selectively operable to form the image either on the entrance slit of a monochromator or on a grating of a monochromator,
   (e) a monochromator having entrance and exit slits and at least two gratings, the surfaces of the gratings being conjugated optically by an optical system located intermediate of the gratings,
   (f) an optical out-system located at the exit slit of the monochromator and
   (g) light detection means including at least one photomultiplier, an image intensifier tube and a camera, whereby the micrographic image of a sample or its spectrum may be visualized and its intensity curve may be recorded,
   (h) said optical out-system having mobile optical elements selectively operable to form on the photocathode of the image intensifier tube an image formed on the surface of the second monochromator grating or an image formed on the exit slit of the monochromator.

2. A Raman microprobe having means for illuminating a sample from a laser source, a microscope for furnishing an enlarged image of the sample, means for selecting the wavelength of light re-emitted by the sample and means for detecting the light selected, said microprobe including a sample illuminating device to render illumination of the sample uniform comprising:
   (a) a first inclined mirror positioned to intercept an incident laser beam originating from a laser source,
   (b) a second mirror positioned to intercept the laser beam reflected by the first mirror, said second mirror being inclined so as to direct the reflected laser beam toward the microscope, the reflected beam being shifted laterally with respect to the incident beam by a distance equal to the distance between the two inclined mirrors,
   (c) a rotatable support for mounting the two mirrors concentric with respect to the incident laser beam and
   (d) annular illuminating means surrounding the microscope for intercepting the reflected laser beam and focusing the reflected beam on the sample.

3. A Raman microprobe as defined in claim 2, further including a mirror located between the wavelength selecting means and the light detecting means operative to permit the selected light to be directed to a photomultiplier or to a multi-channel image detector such as an image intensifier tube.

4. A Raman microprobe as defined in claim 2, wherein the light detecting means includes a monochannel light detector and a multichannel light detector.

5. A Raman microprobe as defined in claim 4, wherein the light detecting means includes a photomultiplier and an image intensifier.

6. A Raman microprobe for the production of micrographic images of the distribution of a polyatomic species in a sample, obtained by isolating a radiation characteristic of the species chosen in the Raman, Stokes or anti-Stokes spectrum with all points of the sample being simultaneously illuminated, or with the sample beng illuminated along a selected straight or curved line, or with selected points of the sample being illuminated by pin-point illumination, said microprobe including:
   (a) a source of laser radiation,
   (b) a sample illuminating device incorporating means for the illumination of a sample completely, or along a selected straight or curved line, or at a selected point,
   (c) a microscope for providing an enlarged image of the sample,
   (d) a wavelength selecting means having entrance and exit slits and at least two gratings, the surfaces of the gratings being conjugated optically by an optical system located intermediate of the gratings,
   (e) an optical transfer system located between the microscope and the wavelength selecting means and having mobile optical elements selectively operable to form the image either on the entrance slit or on a grating of the wavelength selecting means, (f) light detection means for detecting the selected light, including a photomultiplier and an image intensifier tube, and (g) an optical out-system located between the wavelength selecting means and the light detecting means and having mobile optical elements selectively operable to form on the photomultiplier or on the photocathode of the image intensifier tube an image formed either on the surface of a grating or on the exit slit of the wavelength selecting means.

7. A Raman microprobe as defined in claim 2, further including a pulsed laser source and multichannel detection means.

8. A Raman microprobe as defined in claim 2, wherein the wavelength selecting means is operative to:
(a) isolate the characteristic Raman radiation diffused by the sample and
(b) eliminate the laser radiation diffused by the sample without change in wavelength at a rate of rejection at least equal to $10^{31}$ $10$.

9. A Raman microprobe as defined in claim 2, wherein the wavelength selecting means comprises an additive, at least double monochromator having entrance and exit slits and at least two concave holographic gratings the surfaces of which are conjugated optically through the medium of an optical system located intermediate the gratings.

10. A Raman microprobe as defined in claim 9, wherein the projection of intermediate images of the sample is effected successively on the two gratings and the final image is made on a multichannel photoelectric receiver, the entrance pupil of the microscope being conjugated optically with the slits.

11. A Raman microprobe as defined in claim 9, wherein the projection of intermediate images of the sample effected on the slits, the entrance pupil of the microscope being conjugated optically with the gratings.

12. A Raman microprobe as defined in claim 2, further including a mobile mirror permitting direct observation of the sample before selecting the frequency of the re-emitted light.

13. A Raman microprobe as defined in claim 1, wherein a mobile mirror is provided in the optical transfer system which, after rotation, enables a sample illuminated by laser radiation to be studied.

14. A Raman microprobe as defined in claim 1, further comprising means for rapidly detecting and recording a series of images in the course of the development of the sample as a function of time during physicochemical or biological reactions or transformations.

* * * * *

UNITED STATES PATENT OFFICE
CERTIFICATE OF CORRECTION

PATENT NO. : 4,195,930
DATED : April 1, 1980
INVENTOR(S) : Michel M. Delhaye, et al.

It is certified that error appears in the above-identified patent and that said Letters Patent are hereby corrected as shown below:

Column 8, line 50    change "beng" to --being--

Column 9, line 23    change "$10^{31}\ 10$" to --$10^{-10}$--

Column 10, line 6    change "ismade" to --is made--

*Signed and Sealed this*

*Eighth* Day of *July 1980*

[SEAL]

*Attest:*

SIDNEY A. DIAMOND

*Attesting Officer*    *Commissioner of Patents and Trademarks*